United States Patent [19]

Zaiger et al.

[11] Patent Number: Plant 6,747

[45] Date of Patent: Apr. 18, 1989

[54] PEACH TREE "JUNE PRIDE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 129,784

[22] Filed: Dec. 7, 1987

[51] Int. Cl.[4] ..... A01H 5/00

[52] U.S. Cl. ..... Plt./43

[58] Field of Search ..... Plt./41–43

*Primary Examiner*—James R. Feyrer

[57] ABSTRACT

The new and distinct variety of peach tree is large, vigorous, upright in growth, and is a regular and productive bearer of large, firm, yellow flesh, freestone fruit. The fruit is further characterized by sizing relatively uniform throughout the tree, being globose in shape and having yellow skin substantially overspread with red.

1 Drawing Sheet

ORIGIN OF THE VARIETY

The present variety of peach tree was originated by us in the experimental orchard located at Modesto, Calif. from a cross between O'Henry Peach (U.S. Plant Pat. No. 2,964) and June Lady Peach (U.S. Plant Pat. No. 3,022). A large group of seedlings from this cross were planted and grown under careful observation, one such seedling which is the present variety, having been especially desirable with respect to its fruit was selected for asexual reproduction and commercialization.

ASEXUAL REPRODUCTION OF THE VARIETY

The new variety was asexually reproduced by budding in the experimental orchard located at Modesto, Calif. and shows that such reproductions run true to the original tree in all respects.

SUMMARY OF THE VARIETY

The herein claimed new and distinct variety of peach tree is large, vigorous, upright in growth and a regular and productive bearer of large, firm, yellow flesh, freestone fruit having yellow skin substantially overspread with red. The fruit is further chararacterized by being relatively uniform in size throughout the tree, having good storage and shipping quality; and in comparison to June Lady Peach (U.S. Plant Pat. No. 3,022) the new variety has the ability to produce a greater number of large, uniform sized fruit, with a higher degree of attractive red skin color, and ripening in the same maturity season.

PHOTOGRAPHS OF THE VARIETY

The accompanying color photographs show typical foliage and fruit of the present variety with the upper and lower surface of the leaves, an exterior and sectional view of the fruit, with a fruit being divided on its suture plane to reveal flesh coloration and showing a stone remaining in place. The photographic illustrations were taken shortly after being picked at maturity (shipping ripe) and the colors are as nearly true as reasonably possible in a color representation of this type.

DESCRIPTION OF THE VARIETY

The botanical details of the present variety of peach tree, its foliage and fruit are based on observations of specimens grown at Modesto, Calif., with color definitions (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Bearer.*—Regular.
- *Production.*—Productive.

Trunk:
- *Size.*—Medium to large.
- *Texture.*—Shaggy.

Branches:
- *Size.*—Medium to large.
- *Texture.*—Medium rough.
- *Lenticels.*—Medium number. Medium size.
- *Color.*—Grayish brown.

Leaves:
- *Size.*—Large. Average length — 6½" to 7¼". Average width — 1⅜" to 1¾".
- *Texture.*—Smooth.
- *Margin.*—Crenate.
- *Petiole.*—Medium length. Medium thickness.
- *Glands.*—Reniform. Medium size. Numbers vary 1 to 4. Average number 2. Position on base of leaf blade and upper portion of petiole.
- *Color.*—Upper surface — dark green (28-F-8) to (29-F-8). Lower surface — grayish green (28-E-6) to (29-E-7).

Flower buds:
- *Size.*—Small.
- *Form.*—Plump.
- *Pubescence.*—Pubesent.

Flowers:
- *Size.*—Medium. Non-showy.
- *Blooming period.*—Mar. 4, 1986 to Mar. 10, 1986. Varies slightly with climatic conditions.
- *Pollen.*—Present.
- *Color.*—Pink.

Fruit:
- *Maturity when described.*—Firm ripe.
- *Date of first picking.*—June 20, 1986.
- *Date of last picking.*—June 25, 1986.
- *Size.*—Large. Average diameter axially 2⅞" to 3⅜". Average transversely in suture plane 2⅞" to 3⅜".
- *Form.*—Globose.

*Suture.*—Shallow, extends from base to apex.
*Ventral surface.*—Rounded.
*Base.*—Retuse.
*Cavity.*—Rounded — slightly elongated in suture plane. Average depth — 9/16". Average breadth — $1\frac{1}{8}$".
*Apex.*—Rounded to slight point.

Skin:
*Thickness.*—Medium.
*Texture.*—Medium.
*Tendency to crack.*—None.
*Down.*—Short.
*Color.*—Yellow ground color (5-A-6) to (5-A-8). Overspread with red (8-A-8) to (9-A-8).

Flesh:
*Texture.*—Firm.
*Ripens.*—Even.
*Juice.*—Moderate.
*Flavor.*—Subacid to acid.
*Eating quality.*—Good.
*Color.*—Yellow (4-A-5) to (4-A-7). Pit Cavity — red (9-A-8) to (10-A-8).

Stone:
*Type.*—Freestone.
*Size.*—Large. Average length — $1\frac{3}{8}$" to $1\frac{5}{8}$". Average breadth — 15/16" to 1 1/16". Average thickness — $\frac{5}{8}$" to $\frac{7}{8}$".
*Base.*—Straight.
*Apex.*—Acuminate.

*Surface.*—Irregularly furrowed toward apex, pitted toward base.
*Tendency to split.*—Very slight.
*Color.*—Light brown (7-C-5) to (7-D-6).

Use:
*Market.*—Local and long distance. Dessert.

Keeping quality: Good.
Shipping quality: Good.

The present variety of peach tree and its fruit herein described may vary in slight detail due to climatic, soil conditions and cultural practices under which the variety may be grown; the present description is that of the variety grown under ecological conditions at Modesto, Calif.

We claim:

1. A new and distinct variety of peach tree, substantially as illustrated and described, characterized by its large size, vigorous, upright in growth and a regular and productive bearer of large, firm, yellow flesh, freestone fruit, with a high degree of attractive red skin color and good eating, storage and shipping quality; the new variety is further characterized in comparison to June Lady Peach (U.S. Plant Pat. No. 3,022) by having fruit maturing in the same maturity season but having the ability to produce a greater number of larger, uniform sized fruit, with a higher degree of attractive red skin color.

* * * * *

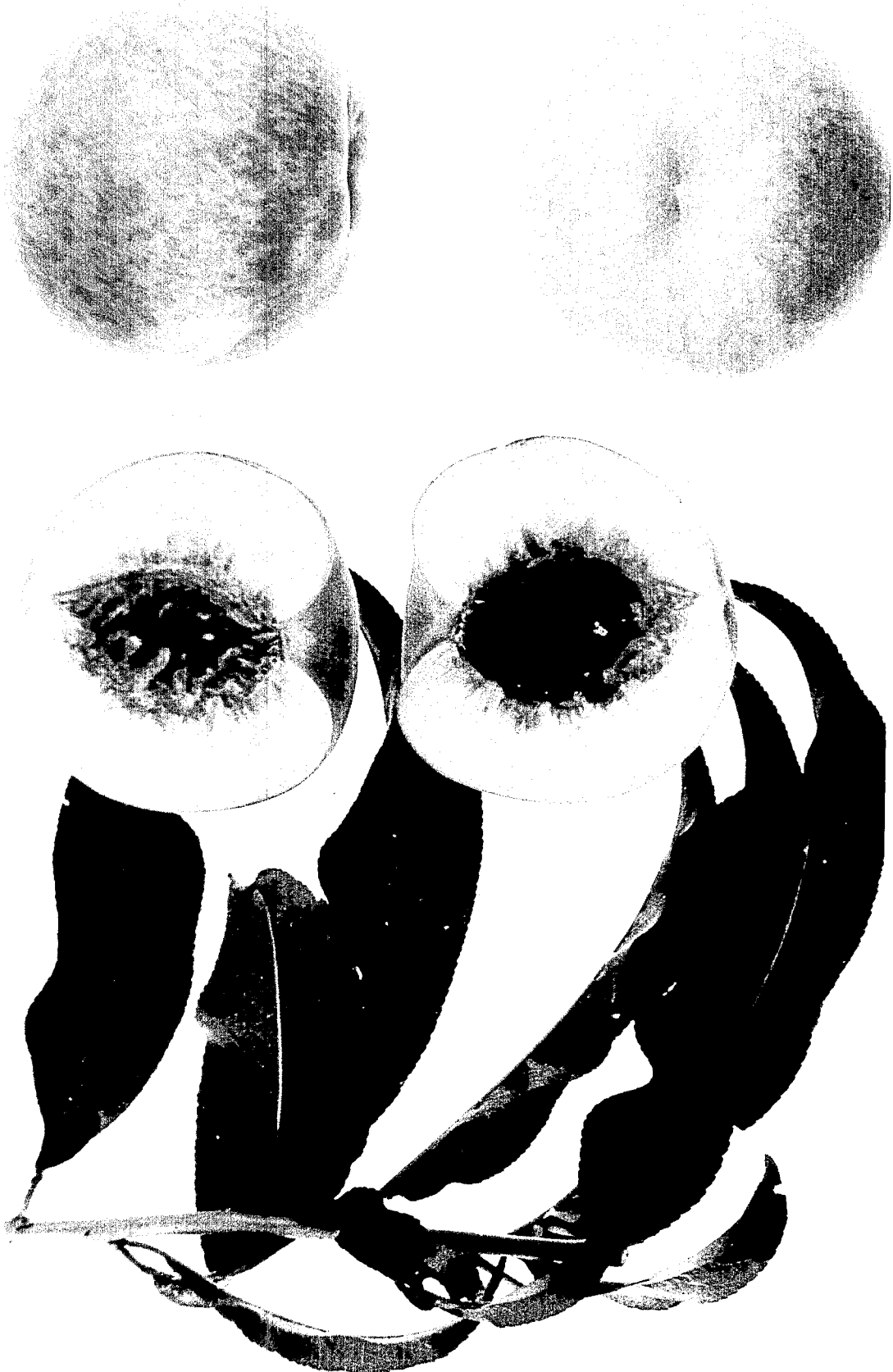

U.S. Patent Apr. 18, 1989 Plant 6,747